(12) United States Patent
Kim et al.

(10) Patent No.: US 7,168,851 B2
(45) Date of Patent: Jan. 30, 2007

(54) APPARATUS AND METHOD FOR MEASURING HEAT DISSIPATION

(75) Inventors: Moo Hwan Kim, Kyungsangbuk-do (KR); Jeong Seob Shin, Kyungsangbuk-do (KR)

(73) Assignee: Postech Foundation, Kyungsangbuk-do (KR)

( * ) Notice: Subject to any disclaimer, the term of this patent is extended or adjusted under 35 U.S.C. 154(b) by 0 days.

(21) Appl. No.: 10/821,882

(22) Filed: Apr. 12, 2004

(65) Prior Publication Data
US 2005/0047477 A1 Mar. 3, 2005

(30) Foreign Application Priority Data
Sep. 1, 2003 (KR) ............... 10-2003-0060696

(51) Int. Cl.
G01N 25/18 (2006.01)
G01N 25/40 (2006.01)
G01K 17/06 (2006.01)

(52) U.S. Cl. .................. 374/44; 374/135; 374/29; 374/31; 374/1

(58) Field of Classification Search ............. 374/10, 374/11, 29–33, 134–135, 43–44, 179, 208, 374/1
See application file for complete search history.

(56) References Cited

U.S. PATENT DOCUMENTS

| | | | | |
|---|---|---|---|---|
| 2,800,793 A * | 7/1957 | Oliver | .................. | 374/33 |
| 3,263,484 A * | 8/1966 | Watson et al. | .................. | 374/11 |
| 3,319,456 A * | 5/1967 | Speros et al. | .................. | 374/11 |
| 3,643,491 A * | 2/1972 | Dell et al. | .................. | 374/11 |
| 3,747,396 A * | 7/1973 | O'Neill | .................. | 374/11 |
| 4,036,051 A * | 7/1977 | Fell et al. | .................. | 374/39 |
| 4,178,800 A * | 12/1979 | Thomann | .................. | 374/33 |
| 4,255,961 A * | 3/1981 | Biltonen et al. | .................. | 374/11 |
| 4,726,688 A * | 2/1988 | Ruel | .................. | 374/29 |
| 5,080,495 A * | 1/1992 | Hashimoto et al. | .................. | 374/43 |
| 5,672,289 A * | 9/1997 | O'Neill | .................. | 219/497 |
| 5,967,659 A * | 10/1999 | Plotnikov et al. | .................. | 374/11 |
| 6,170,984 B1* | 1/2001 | Schawe et al. | .................. | 374/10 |
| 6,189,367 B1* | 2/2001 | Smith et al. | .................. | 73/19.03 |
| 6,238,085 B1* | 5/2001 | Higashi et al. | .................. | 374/10 |
| 6,370,939 B1* | 4/2002 | Smith et al. | .................. | 73/19.03 |
| 6,561,692 B1* | 5/2003 | Danley | .................. | 374/29 |
| 6,583,391 B1* | 6/2003 | Jorimann et al. | .................. | 219/497 |
| 6,632,015 B1* | 10/2003 | Nagasawa | .................. | 374/11 |
| 6,843,595 B1* | 1/2005 | Danley | .................. | 374/10 |
| 2003/0043879 A1* | 3/2003 | Tanaka et al. | .................. | 374/31 |

FOREIGN PATENT DOCUMENTS

| | | | |
|---|---|---|---|
| JP | 57142525 | * | 9/1982 |
| JP | 40996874 A | * | 7/1987 |
| JP | 11160261 A | * | 6/1999 |
| SU | 989419 A | * | 1/1983 |

* cited by examiner

*Primary Examiner*—Gail Verbitsky
(74) *Attorney, Agent, or Firm*—Bacon & Thomas, PLLC

(57) ABSTRACT

An apparatus for measuring heat dissipation of a target heating element includes a reference heating element for emitting heat; a control unit; and a pair of temperature measuring devices for measuring representative temperatures of the target and the reference heating element and transmitting to the control unit signals indicating the representative temperatures. The reference heating element has an outer configuration and sizes substantially identical to those of the target heating element. The control unit controls the reference heating element such that the representative temperature of the reference heating element becomes substantially identical to that of the target heating element.

9 Claims, 3 Drawing Sheets

APPARATUS AND METHOD FOR MEASURING HEAT DISSIPATION

FIELD OF THE INVENTION

The present invention relates to an apparatus and method for measuring heat dissipation, which is capable of precisely measuring the heat dissipation of a heat dissipating element with ease by using a reference heat dissipating element.

BACKGROUND OF THE INVENTION

There have been a growing interest in and active research and development of cooling devices or heat exchangers applied to electrical and electronic appliances. Under the circumstances, the need to precisely and easily measure or calculate heat dissipation of a heat dissipating element incorporated in the cooling device or the heat exchanger is continuously increasing in the field of quality control, performance test and the like.

A conventional method for measuring the heat dissipation of an object (heating element) is to measure a variation in heat quantity of a heat carrying fluid (or secondary fluid), e.g., water or air, which enters and leaves a vessel accommodating the object. That is, when the heat dissipation is measured in accordance with the conventional method, a heating element is disposed in a vessel or a passage through which the heat carrying fluid flows to absorb heat from the heating element. Then, the heat carrying fluid's thermophysical properties including a temperature change owing to heat transfer between the heat carrying fluid and the heating element, specific heat, flow rate and the like are measured, and the variation in heat quantity (Qv) of the heat carrying fluid is obtained by using the following formula:

$$Qv = mf \times c \times (T2 - T1) \quad \text{Eq. 1}$$

where mf is a mass flow rate (a product of volumetric flow rate and density); c is a specific heat; T1 is an inflow temperature of the heat carrying fluid; and T2 is an outflow temperature of the heat carrying fluid.

However, determining the heat carrying fluid's thermophysical properties is very difficult especially when the amount of the heat dissipation is very little. Further, since the temperature of the heat carrying fluid is higher (or lower) than that of the surroundings of the vessel, the heat carrying fluid loses heat to (or absorbs heat from) the surroundings. Although the vessel or the passage may be insulated in an attempt to prevent this heat loss (or heat absorption) problem, the heat loss (or absorption) cannot be completely prevented. Thus, it is inevitable that the heat quantity variation as calculated above includes a heat quantity variation owing to the heat loss to (or heat absorption from) the surroundings as well as a heat quantity variation owing to the heat transfer between the heat carrying fluid and the heating element.

As described above, the conventional heat dissipation measuring method relies on the heat carrying fluid's thermophysical properties, which are measured with difficulty, and which are susceptible to an unavoidable heat loss the amount of which cannot be precisely measured. Accordingly, the conventional method presents such drawbacks of requiring considerable time, efforts and costs, necessitating complex equipments and methods for measuring the heat carrying fluid's thermophysical properties, and resulting in inaccurate measurement results.

SUMMARY OF THE INVENTION

It is, therefore, an object of the present invention to provide an improved apparatus and method for readily and precisely measuring heat dissipation of a heating element without measuring heat carrying fluid's thermophysical properties and being disturbed by a heat loss (or heat absorption) problem even when the amount of the heat dissipation is very little.

In accordance with one aspect of the invention, there is provided an apparatus for measuring heat dissipation of a target heating element, including: a reference heating element for emitting heat; a control unit; and a pair of temperature measuring devices for measuring representative temperatures of the target and the reference heating element and transmitting to the control unit signals indicating the representative temperatures, wherein the reference heating element has an outer configuration and sizes substantially identical to those of the target heating element, and wherein the control unit controls the reference heating element such that the representative temperature of the reference heating element becomes substantially identical to that of the target heating element.

In accordance with another aspect of the invention, there is provided a method for measuring heat dissipation of a target heating element, including the steps of: detecting and comparing representative temperatures of the target heating element and a reference heating element for emitting heat; controlling the reference heating element such that the representative temperatures of the target and the reference heating element become substantially identical to each other; and determining a heating value of the reference heating element as the heat dissipation of the target heating element when the representative temperatures of the target and the reference heating element are substantially identical to each other, wherein the reference heating element has an outer configuration and sizes substantially identical to those of the target heating element.

In accordance with still another aspect of the invention, there is provided an apparatus for measuring heat dissipation of a target heating element, including: means for detecting representative temperatures of the target heating element and a reference heating element; and means for comparing the representative temperatures, controlling the reference heating element such that the representative temperatures become substantially identical to each other, and determining heating value of the reference heating element as the heat dissipation of the target heating element when the representative temperatures are substantially identical to each other, wherein the reference heating element has an outer configuration and sizes substantially identical to those of the target heating element.

BRIEF DESCRIPTION OF THE DRAWINGS

The above and other objects and features of the present invention will become apparent from the following description of preferred embodiments given in conjunction with the accompanying drawings, in which.

DETAILED DESCRIPTION OF THE PREFERRED EMBODIMENTS

Figure 1:
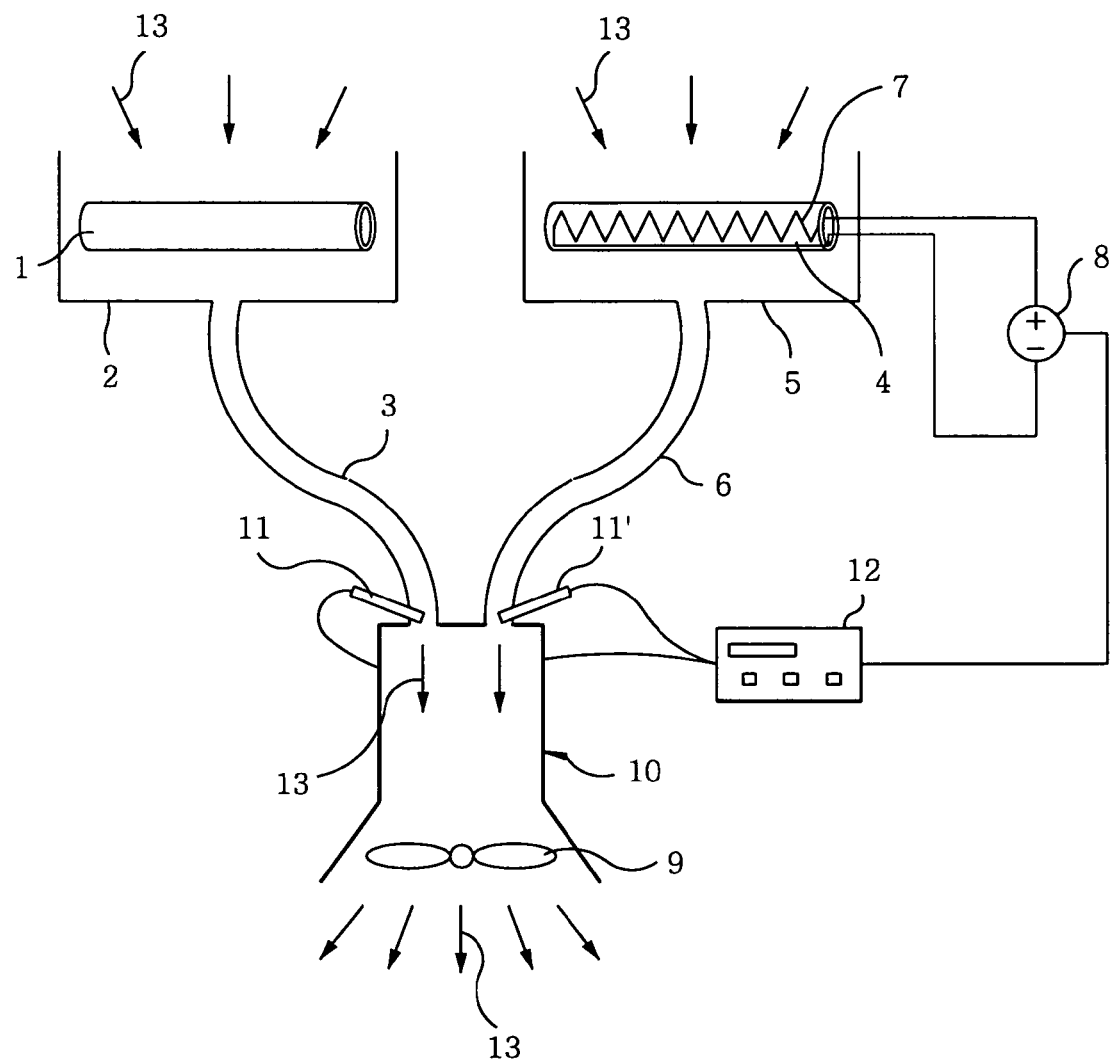
FIG. 1 is a schematic view of an apparatus for measuring heat dissipation in accordance with a first preferred embodiment of the present invention.
Figure 2:
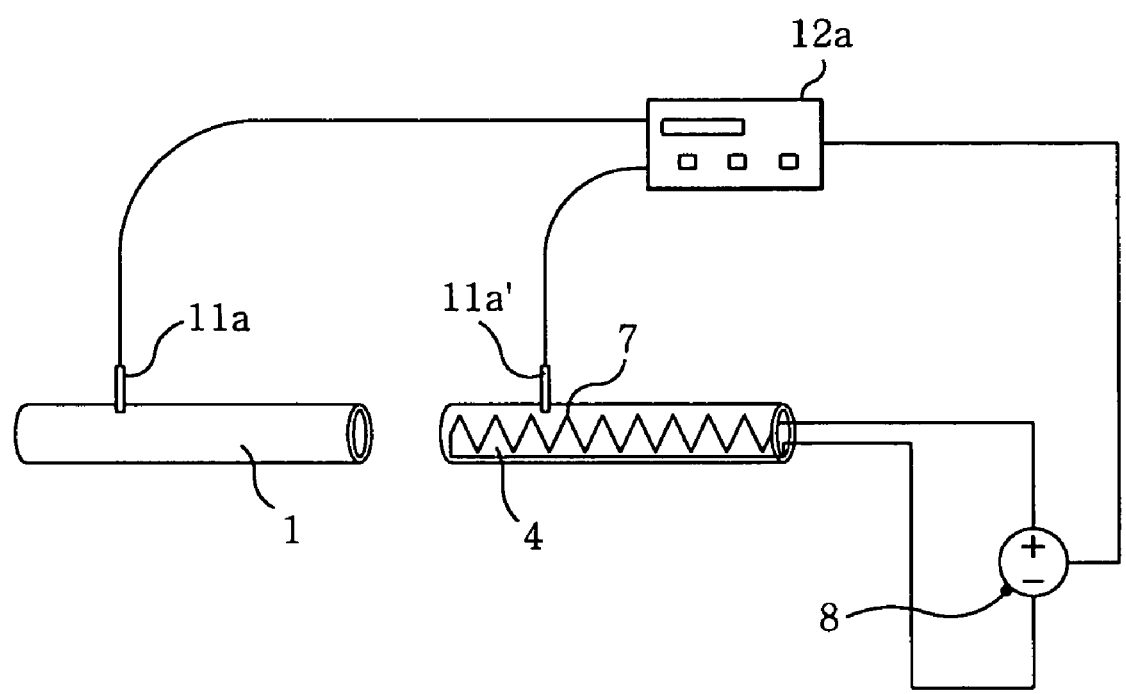
FIG. 2 presents a schematic view of an apparatus for measuring heat dissipation in accordance with a second preferred embodiment of the present invention.
Figure 3:
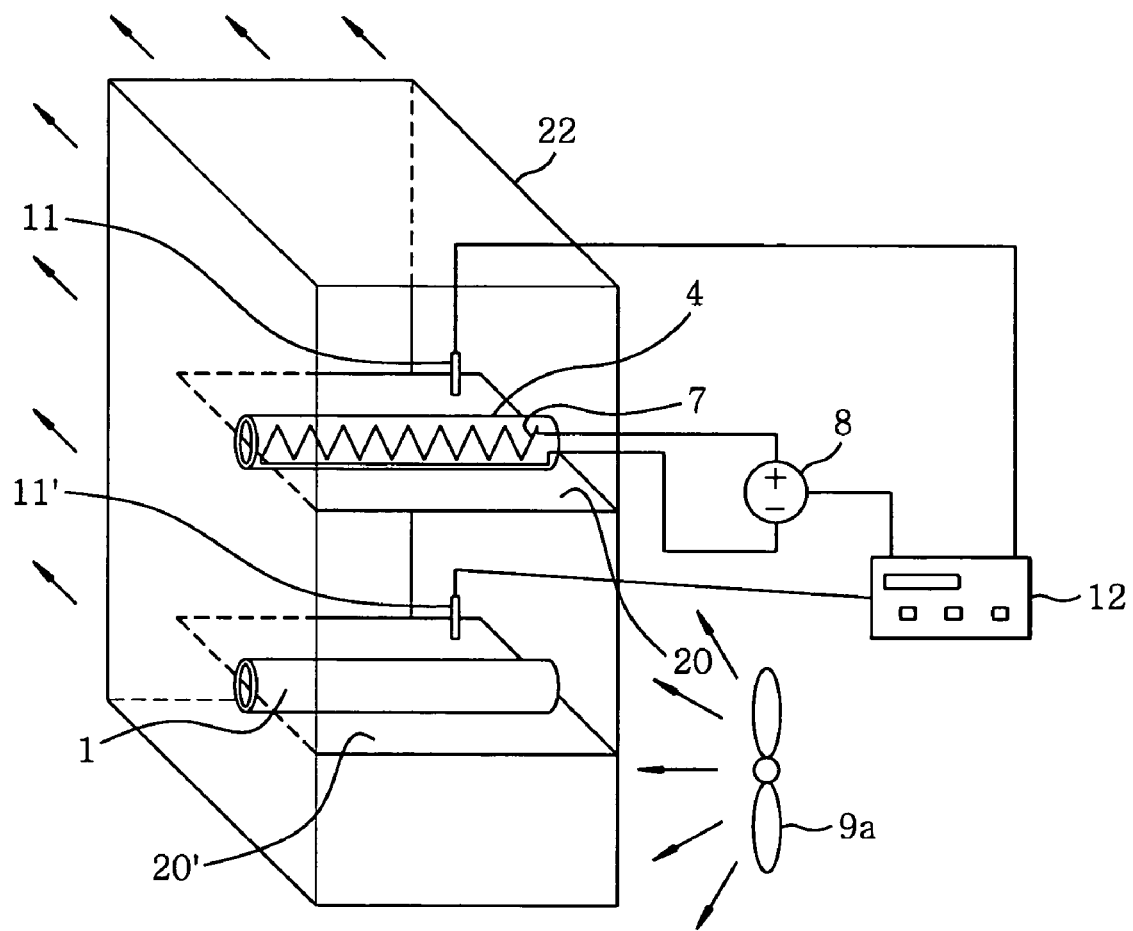
FIG. 3 illustrates a schematic view of an apparatus for measuring heat dissipation in accordance with a third preferred embodiment of the present invention.

Preferred embodiments of the present invention will now be described in detail with reference to the accompanying drawings, wherein like parts appearing FIGS. 1 to 3 are represented by like reference numerals.

The present invention is based on the concept that heating values or heat dissipations of two objects, which have a same outer configuration and sizes and which are in same surroundings, are identical to each other if their representative temperatures are equal to each other. And various structures and methods for determining the representative temperatures are offered in the following preferred embodiments.

Referring to FIG. 1, there is schematically illustrated an apparatus for measuring heat dissipation of an object (heating element) in accordance with a first preferred embodiment of the present invention. As shown in FIG. 1, the apparatus for measuring heat dissipation of an object includes a reference heating element 4 which has an outer configuration and sizes substantially identical to those of a target heating element 1 whose heat dissipation is to be measured. The target heating element 1 may be any object emitting heat, such as a portion of a pipe through which a condensed refrigerant flows. Further, any object whose outer configuration and sizes are substantially identical to those of the target heating element 1 and whose heating value is variable and known or easily obtained can be used as the reference heating element 4. The reference heating element 4 is provided with an electrical heater 7 which is electrically connected to a variable power source 8 and, thus its heating value can be calculated by using a power supplied to the electrical heater 7.

Further, the apparatus for measuring heat dissipation of an object includes vessels 2 and 5 in which the target and the reference heating element 1 and 4 are disposed under a same condition. The vessels 2 and 5 have ports respectively on their bottoms, and are substantially identical to each other in geometry and material. The ports of the vessels 2 and 5 are connected to a flow generator 10 through ducts 3 and 6, which are also substantially identical to each other in geometry and material. The flow generator 10 with a chamber 10a and a fan 9 draws a heat carrying fluid (or secondary fluid) 13, e.g., water or air, from the vessels 2 and 5 through the ducts 3 and 6 with a same suction force. The heat carrying fluid 13 is supplied to the vessels 2 and 5 at a same rate from the surroundings or by a supplier (not shown) and discharged therefrom through the ports at a same rate by the flow generator 10. Further, the vessels 2 and 5 are disposed in substantially identical surroundings and the ducts 3 and 6 are also disposed in substantially identical surroundings.

To measure temperatures, i.e., the representative temperatures, of the heat carrying fluids 13 flowing in the ducts 3 and 6, temperature measuring devices 11 and 11', e.g., thermometers, are installed in the ducts 3 and 6 respectively in such a manner that a travel distance of the heat carrying fluid 13 in the duct 3 from the port of the vessel 2 to the temperature measuring device 11 is equal to that of the heat carrying fluid 13 in the duct 6 from the port of the vessel 5 to the temperature measuring device 11'. The temperature measuring devices 11 and 11' transmit to a control unit 12 signals indicating temperatures measured thereat.

The control unit 12 controls the variable power supply 8 in such a manner that the temperatures measured by the temperature measuring devices 11 and 11' become identical to each other. For example, if the temperature of the heat carrying fluid 13 flowing in the duct 3 is greater than that of the heat carrying fluid 13 flowing in the duct 6, the control unit 12 controls the variable power supply 8 to increase power supplied to the heater 7 by a desired level. In contrast, if the temperature of the heat carrying fluid 13 flowing in the duct 3 is less than that of the heat carrying fluid 13 flowing in the duct 6, the control unit 12 controls the variable power supply 8 to reduce power supplied to the heater 7 by a desired level. When the temperatures become substantially identical to each other, the control unit 12 calculates the heating value of the reference heating element 4 by using the power supplied to the heater 7 at that time. The heating value of the reference heating element 4 thus obtained is regarded as the heat dissipation of the target heating element 1.

Referring to FIG. 2, there is schematically illustrated an apparatus for measuring heat dissipation of an object in accordance with a second preferred embodiment of the present invention, wherein like parts to those of the first embodiment are represented by like reference characters and detailed descriptions thereof will be omitted. The apparatus of the second preferred embodiment is identical to the apparatus of the first preferred embodiment except that the representative temperatures are average surface temperatures measured on surfaces of the target heating element 1 and the reference heating element 4.

The apparatus of the second preferred embodiment includes temperature measuring devices 11a and 11a' for measuring surface temperatures of the target heating element 1 and the reference heating element 4. The temperature measuring devices 11a and 11a' have, for example, plural number of thermocouples attached on the surfaces of the target heating element 1 and the reference heating element 4 at plural corresponding locations, respectively. The temperature measuring devices 11a and 11a' transmit to a control unit 12a signals indicating temperatures measured thereat. The control unit 12a calculates the average surface temperatures of the target heating element 1 and the reference heating element 4, and controls the variable power supply 8 in such a manner that the average surface temperature of the target heating element 1 becomes substantially identical to that of the reference heating element 4. For example, if the average surface temperature of the target heating element 1 is greater than that of the reference heating element 4, the control unit 12a controls the variable power supply 8 to increase power supplied to the heater 7 by a desired level. In contrast, if the average surface temperature of the object heating element 1 is less than that of the reference heating element 4, the control unit 12 controls the variable power supply 8 to reduce power supplied to the heater 7 by a desired level. When the average surface temperatures become substantially identical to each other, the control unit 12a calculates the heating value of the reference heating element 4 by using the power supplied to the heater 7 at that time. The heating value of the reference heating element 4 thus obtained is regarded as the heat dissipation of the target heating element 1.

Referring to FIG. 3, an apparatus for measuring heat dissipation of an object in accordance with a third preferred embodiment of the present invention will now be described, wherein like parts to those of the first embodiment are represented by like reference characters and detailed descriptions thereof will be omitted.

In this preferred embodiment, the representative temperatures are measured from fins 20 and 20' attached to the target and the reference heating element 1 and 4. The apparatus of the third preferred embodiment includes a duct 22 in which the target 1 and the reference heating element 1 and 4 are horizontally installed parallel to each other. The fins 20 and 20' are horizontally attached to or in contact with the target and the reference heating element 1 and 4, respectively. Preferably, a fan 9a is installed in front of the duct 22 in order to supply airflow (or the heat carrying fluid) thereto. The temperature measuring devices 11 and 11' are sticked to the fins 20 and 201 at corresponding locations, respectively. The temperature measuring devices 11 and 11' transmit to the control unit 12 signals indicating temperatures (the representative temperatures) measured thereat. The control unit 12 controls the variable power supply 8 in the manner used in the first preferred embodiment. When the measured temperatures become identical to each other, the control unit calculates the heating value of the reference heating element 4 by using the power supplied to the heater 7 at that time. The heating value of the reference heating element 4 thus obtained is regarded as the heat dissipation of the target heating element 1.

As described above, in the preferred embodiments of the present invention, the heat dissipation of the target heating element can be measured by comparing the representative temperatures of the target and the reference heating element and calculating the heating value of the reference heating element. Thus, the apparatus for measuring heat dissipation of an object in accordance with the present invention does not require the insulation of a vessel accommodating the target heating element and the heat carrying fluid's thermophysical properties. Accordingly, easy and precise measurement of heat dissipation of an object can be effectively conducted.

While the invention has been shown and described with respect to the preferred embodiments, it will be understood by those skilled in the art that various changes and modifications may be made without departing from the spirit and scope of the invention as defined in the following claims.

What is claimed is:

1. An apparatus for measuring heat dissipation of a target heating element, comprising:
    a reference heating element for emitting heat;
    a control unit;
    a pair of temperature measuring devices for measuring representative temperatures of the target and the reference heating elements and transmitting to the control unit signals indicating the representative temperatures;
    a first vessel for accommodating the target heating element;
    a second vessel for accommodating the reference heating element;
    a first duct connected to the first vessel;
    a second duct connected to the second vessel; and
    a flow generator for drawing heat carrying fluids in the first and the second vessels through the first and the second ducts at a same rate,
    wherein the reference heating element has an outer configuration and sizes substantially identical to those of the target heating element, and wherein the control unit controls the reference heating element such that the representative temperature of the reference heating element becomes substantially identical to that of the target heating element,
    wherein the reference heating element is provided with an electrical heater controlled by the control unit,
    wherein the control unit compares the representative temperatures of the target and the reference heating elements and calculates heating value of the reference heating element by using a power supplied to the electrical heater when the representative temperatures are substantially equal to each other, and
    wherein the temperature measuring devices are installed at substantially corresponding locations in the first and the second ducts, respectively, and measures temperatures of the heat carrying fluids in the first and the second duct as the representative temperatures, and wherein the first and the second vessels are substantially identical to each other in geometry, and the first and the second duct are substantially identical to each other in geometry.

2. The apparatus of claim 1, wherein the heat carrying fluids in the first and the second ducts are air.

3. An apparatus for measuring heat dissipation of a target heating element, comprising:
    a reference heating element for emitting heat;
    a control unit; and
    a pair of temperature measuring devices for measuring representative temperatures of the target and the reference heating elements and transmitting to the control unit signals indicating the representative temperatures;
    wherein the reference heating element has an outer configuration and sizes substantially identical to those of the target heating element, and wherein the control unit controls the reference heating element such that the representative temperature of the reference heating element becomes substantially identical to that of the target heating element,
    wherein the reference heating element is provided with an electrical heater controlled by the control unit,
    wherein the control unit compares the representative temperatures of the target and the reference heating elements and calculates heating value of the reference heating element by using a power supplied to the electrical heater when the representative temperatures are substantially equal to each other, and
    wherein the temperature measuring devices are attached on surfaces of the target and the reference heating elements and measure average surface temperatures of the target and the reference heating elements as the representative temperatures.

4. The apparatus of claim 3, wherein the temperature measuring devices are a thermocouple.

5. An apparatus for measuring heat dissipation of a target heating element, comprising:
    a reference heating element for emitting heat;
    a control unit;
    a pair of temperature measuring devices for measuring representative temperatures of the target and the reference heating elements and transmitting to the control unit signals indicating the representative temperatures;
    a duct for accommodating the target and the reference heating element; and
    a pair of fins for being in contact with or being attached to the target and the reference heating elements, respectively,
    wherein the reference heating element has an outer configuration and sizes substantially identical to those of the target heating element, and wherein the control unit controls the reference heating element such that the representative temperature of the reference heating element becomes substantially identical to that of the target heating element,
    wherein the reference heating element is provided with an electrical heater controlled by the control unit,
    wherein the control unit compares the representative temperatures of the target and the reference heating elements and calculates heating value of the reference heating element by using a power supplied to the electrical heater when the representative temperatures are substantially equal to each other, and wherein the temperature measuring devices measure temperatures of the fins at substantially corresponding locations of the fins, respectively as the representative temperatures.

6. The apparatus of claim 5, further comprising a flow generator for supplying a heat carrying fluid into the duct.

7. A method for determining heat dissipation of a target heating element, comprising the steps of:

detecting and comparing representative temperatures of the target heating element and a reference heating element for emitting heat;

controlling the reference heating element such that the representative temperatures of the target and the reference heating elements become substantially identical to each other; and determining the heat dissipation of the target heating element by using a heating value of the reference heating element when the representative temperatures of the target and the reference heating elements are substantially identical to each other, wherein the reference heating element has an outer configuration and sizes substantially identical to those of the target heating element, and wherein the representative temperature of the target heating element is measured from a heat carrying fluid which has flown past the target heating element and the representative temperature of the reference heating element is measured from a heat carrying fluid which has flown past the reference heating element.

8. A method for determining heat dissipation of a target heating element, comprising the steps of:

detecting and comparing representative temperatures of the target heating element and a reference heating element for emitting heat;

controlling the reference heating element such that the representative temperatures of the target and the reference heating elements become substantially identical to each other; and determining the heat dissipation of the target heating element by using a heating value of the reference heating element when the representative temperatures of the target and the reference heating elements are substantially identical to each other, wherein the reference heating element has an outer configuration and sizes substantially identical to those of the target heating element, and wherein the representative temperature of the target heating element is an average surface temperature of the target heating element, and the representative temperature of the reference heating element is an average surface temperature of the reference heating element.

9. A method for determining heat dissipation of a target heating element, comprising the steps of:

detecting and comparing representative temperatures of the target heating element and a reference heating element for emitting heat;

controlling the reference heating element such that the representative temperatures of the target and the reference heating elements become substantially identical to each other; and determining the heat dissipation of the target heating element by using a heating value of the reference heating element when the representative temperatures of the target and the reference heating elements are substantially identical to each other, wherein the reference heating element has an outer configuration and sizes substantially identical to those of the target heating element, and wherein the representative temperatures of the target and the reference heating elements are measured at substantially corresponding locations of fins, which are in contact with or attached to the target and the reference heating element, respectively.

* * * * *